US010544072B2

(12) United States Patent
Schreck et al.

(10) Patent No.: US 10,544,072 B2
(45) Date of Patent: Jan. 28, 2020

(54) CONTINUOUS PROCESSES FOR THE HIGHLY SELECTIVE CONVERSION OF ALDOHEXOSE-YIELDING CARBOHYDRATE TO ETHYLENE GLYCOL

(71) Applicant: Iowa Corn Promotion Board, Johnston, IA (US)

(72) Inventors: David James Schreck, Lake City, MN (US); Ray Chrisman, Midland, MI (US); Brooke Albin, Charleston, WV (US); Nye Clinton, Hurricane, WV (US); Marion McKinley Bradford, Hendersonville, NC (US); Donald Bunning, South Charleston, WV (US)

(73) Assignee: Iowa Corn Promotion Board, Johnston, IA (US)

( * ) Notice: Subject to any disclaimer, the term of this patent is extended or adjusted under 35 U.S.C. 154(b) by 0 days.

(21) Appl. No.: 15/612,700

(22) Filed: Jun. 2, 2017

(65) Prior Publication Data

US 2017/0349513 A1 Dec. 7, 2017

Related U.S. Application Data

(60) Provisional application No. 62/345,399, filed on Jun. 3, 2016.

(51) Int. Cl.
| | | |
|---|---|---|
| *B01J 21/02* | (2006.01) | |
| *B01J 21/12* | (2006.01) | |
| *B01J 23/46* | (2006.01) | |
| *B01J 23/89* | (2006.01) | |
| *B01J 35/10* | (2006.01) | |
| *C07C 29/00* | (2006.01) | |
| *C07C 31/10* | (2006.01) | |
| *C07C 31/20* | (2006.01) | |
| *B01J 23/889* | (2006.01) | |
| *C07C 29/141* | (2006.01) | |
| *C07C 29/145* | (2006.01) | |
| *C07C 31/125* | (2006.01) | |

(52) U.S. Cl.
CPC ............ *C07C 29/145* (2013.01); *B01J 21/02* (2013.01); *B01J 21/12* (2013.01); *B01J 23/462* (2013.01); *B01J 23/8896* (2013.01); *B01J 23/892* (2013.01); *B01J 35/1019* (2013.01); *B01J 35/1042* (2013.01); *C07C 29/141* (2013.01); *C07C 31/10* (2013.01); *C07C 31/125* (2013.01); *C07C 31/202* (2013.01); *C07C 29/00* (2013.01); *Y02P 20/52* (2015.11)

(58) Field of Classification Search
CPC ........ B01J 21/02; B01J 23/462; B01J 23/892; C07C 29/145; C07C 31/10; C07C 31/125; C07C 31/202; C07C 29/00; Y02P 20/52
See application file for complete search history.

(56) References Cited

U.S. PATENT DOCUMENTS

| | | | |
|---|---|---|---|
| 2,993,755 A | 7/1961 | Redanz et al. | |
| 3,077,379 A | 2/1963 | Pilloton et al. | |
| 5,210,335 A * | 5/1993 | Schuster ................. | C07C 29/00 |
| | | | 568/861 |
| 5,641,872 A | 6/1997 | Darsow | |
| 6,476,218 B1 | 11/2002 | Choque et al. | |
| 6,534,441 B1 | 3/2003 | Bartley et al. | |
| 6,649,754 B1 | 11/2003 | Mohr et al. | |
| 8,222,462 B2 | 7/2012 | Kalnes et al. | |
| 8,222,463 B2 | 7/2012 | Kalnes et al. | |
| 8,222,464 B2 | 7/2012 | Kalnes et al. | |
| 8,222,465 B2 | 7/2012 | Kalnes et al. | |
| 8,323,937 B2 | 12/2012 | Zhang et al. | |
| 8,816,068 B2 | 8/2014 | Kuusisto et al. | |
| 9,399,610 B2 * | 7/2016 | Schreck ................... | B01J 21/02 |
| 10,131,600 B2 | 11/2018 | Van Der Waal et al. | |
| 10,233,138 B2 | 3/2019 | Van Der Waal | |
| 2008/0103339 A1 | 5/2008 | Bloom | |
| 2009/0005553 A1 | 1/2009 | Hassan et al. | |
| 2009/0203874 A1 | 8/2009 | Loffler et al. | |
| 2011/0312487 A1 | 12/2011 | Chen et al. | |
| 2011/0312488 A1 | 12/2011 | Chen et al. | |
| 2012/0172633 A1 | 7/2012 | Zhang et al. | |
| 2013/0338406 A1 | 12/2013 | Liu et al. | |
| 2015/0218064 A1 | 8/2015 | Birkhoff et al. | |
| 2015/0329449 A1 | 11/2015 | Schreck et al. | |
| 2016/0207856 A1 | 7/2016 | Van Der Heide et al. | |
| 2018/0002259 A1 | 1/2018 | Van Der Waal et al. | |
| 2011/8036242 | 12/2018 | Van Der Heide et al. | |
| 2018/0362424 A1 | 12/2018 | Chewter et al. | |
| 2019/0062243 A1 | 2/2019 | Muthusamy et al. | |
| 2019/0062244 A1 | 2/2019 | Perez Golf et al. | |

FOREIGN PATENT DOCUMENTS

| | | | |
|---|---|---|---|
| WO | 2015028593 A1 | 3/2015 | |
| WO | WO-2015028593 A1 * | 3/2015 | ........... C07C 29/132 |
| WO | 2016114659 | 7/2016 | |
| WO | 2016114660 | 7/2016 | |
| WO | 2016114661 | 7/2016 | |
| WO | 2017097847 A1 | 6/2017 | |

OTHER PUBLICATIONS

Ooms et al., "Conversion of sugars to ethylene glycol with nickel tungsten carbide in a fed-batch reactor: high productivity and reaction network elucidation", "Green Chem", Jan. 1, 2014, pp. 695-707, vol. 16, Publisher: The Royal Society of Chemistry.

* cited by examiner

*Primary Examiner* — Pancham Bakshi
*Assistant Examiner* — Mark R Luderer
(74) *Attorney, Agent, or Firm* — Davis, Brown, Koehn, Shors & Roberts, P.C.; Matthew W. Coryell

(57) ABSTRACT

Continuous processes for making ethylene glycol form aldohexose-yielding carbohydrates are disclosed which enhance the selectivity to ethylene glycol.

19 Claims, 1 Drawing Sheet

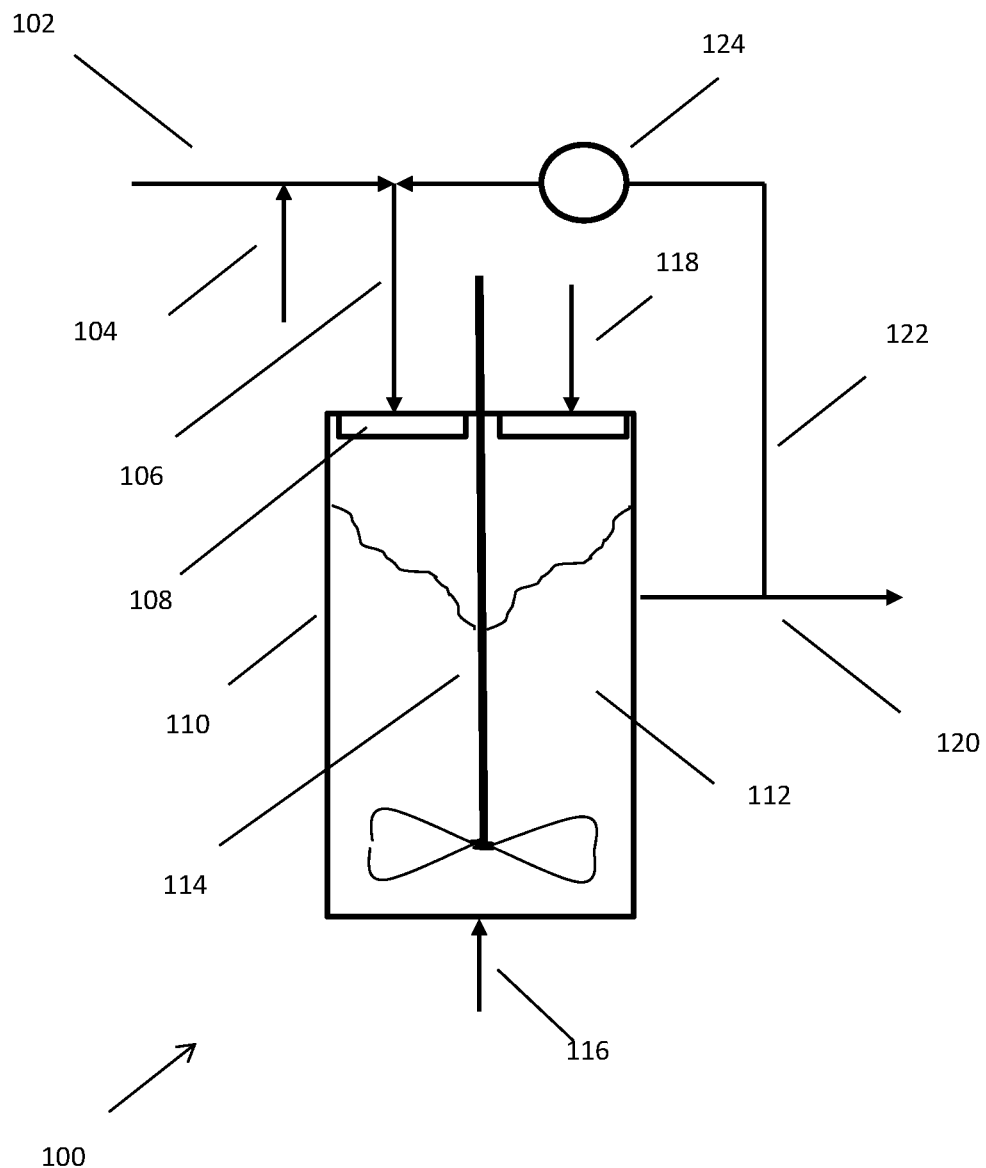

CONTINUOUS PROCESSES FOR THE HIGHLY SELECTIVE CONVERSION OF ALDOHEXOSE-YIELDING CARBOHYDRATE TO ETHYLENE GLYCOL

CROSS REFERENCE TO RELATED PATENT APPLICATIONS

This Application claims the benefit of U.S. Provisional Application No. 62/345,399, filed Jun. 3, 2016, which is incorporated by reference in its entirety.

FIELD OF THE INVENTION

This invention pertains to processes for the production of ethylene glycol, particularly high-efficiency, continuous processes for the conversion of aldohexose-yielding carbohydrate to ethylene glycol.

BACKGROUND

Ethylene glycol is a valuable commodity chemical that has a broad range of uses as both a building block for other materials such as polyethylene terephthalate (PET) and for its intrinsic properties such as for antifreeze. Ethylene glycol demand is substantial, making it one of the largest volume organic chemicals produced in the world. It is currently made by multistep processes which start with ethylene derived from hydrocarbon feedstocks.

Proposals have been made to manufacture ethylene glycol from renewable resources such as carbohydrates. See, for instance, U.S. Pat. No. 5,210,335; EP 2419393; U.S. Published Pat. Appl. 2012/0172633; and Green Chem., 2014, 16, 695-707. Until recently, the proposed processes for manufacturing ethylene glycol from carbohydrates have suffered from extremely low selectivities to ethylene glycol. More recent proposals have focused on the use of two catalysts for the conversion of carbohydrates to ethylene glycol. One catalyst effects a retro-aldol reaction, and the second is used for hydrogenation. Thus, for instance, an aldohexose is converted to glycolaldehyde and erythrose, and the glycolaldehyde is in turn hydrogenated to ethylene glycol. Erythrose can undergo additional retro-aldol reaction to provide two more molecules of glycolaldehyde. Although the processes provide higher selectivity to ethylene glycol, a need still remains to provide a process that would be commercially competitive with conventional processes using ethylene as the feedstock.

Schreck, et al., in U.S. Published Pat. Appl. 2015/0329449, disclose improved, continuous processes for the conversion of carbohydrates to ethylene glycol and propylene glycol. They disclose using a reactor for the conversion of carbohydrates to the glycols which has a first zone comprising a retro-aldol catalyst and a second zone comprising a retro-aldol and reducing catalyst. Where the feed is an aldose, glycolaldehyde from the retro-aldol reaction is hydrogenated in the second zone of the reactor to ethylene glycol. They also disclose using ketose as the carbohydrate to produce propylene glycol.

Nevertheless, challenges still remain to further enhance the selectivity of the conversion of carbohydrates to glycols, especially to ethylene glycol. These challenges are not insignificant due to the myriad of reactions that can occur under the conditions required for the retro-aldol reaction and for the hydrogenation, including, but not limited to, hydrogenation of the hexose to hexitol and the formation of side products such as methane, methanol, ethanol, propanol, glycerin, 1,2-butanediol, threitol, and humins. Although some side products may be marketable, their recovery to meet merchant grade specification can be costly. Moreover, glycolaldehyde is highly reactive.

SUMMARY

By this invention, continuous processes are provided that enhance the selectivity of a retro-aldol and hydrogenation conversion of aldohexose-yielding carbohydrate to ethylene glycol.

In accordance with the first broad aspect of this invention, a rapid heating of a carbohydrate being fed into a reaction zone can reduce the production of hexitol and other side products such as propylene glycol. The mechanism by which the rapid heating of the carbohydrate feed results in the enhance selectivity of conversion to ethylene glycol is not fully understood. Without wishing to be limited to theory, it is believed, in part, that at temperatures above 230° C. in the presence of retro-aldol catalyst, the rate of the retro-aldol conversion of aldoses to glycolaldehyde is sufficiently rapid that preferentially aldose is reacted to make glycolaldehyde and intermediates that can provide ethylene glycol in comparison to other reactions that can generate side products or reduce selectivity of conversion to ethylene glycol.

Measuring directly the rate of heating of the carbohydrate feed containing the aldohexose-yielding carbohydrate is problematic due to the speed at which the heating occurs. The problem of temperature measurement is further confounded by the heat and mass transfer through the fluid which is being heated. The heat and mass transfer parameters within a given fluid will depend upon many factors including, but not limited to, the method of heating, the temperature differential, and the physical structure of the zone in which the heating is occurring. Moreover, the analytical techniques to measure temperatures essentially in all regions of the fluid are practically unavailable. Accordingly, ascertaining whether or not the rate of heating is sufficient can only practically be done by reference to the relative formation of certain compounds generated in the practice of the process. Nevertheless, it is believed that the rate of heating is sufficient to raise the temperature of the entire carbohydrate feed from about 170° C. to at least 230° C. in less than about 10 seconds, and more preferably in less than about 5 seconds, and in some instances less than about 3 seconds, and in some other instances less than about 1 second.

The temperature range through which the carbohydrate feed is to be rapidly heated in accordance with processes of this invention is from below 170° C. to above 230° C. In some instances, the carbohydrate feed may be at a temperature below about 150° C., or even below about 100° C., when the rapid heating commences. In some instances it is preferred that where the carbohydrate feed contains retro-aldol catalyst, the rapid heating of the carbohydrate feed commences prior to about 100° C.

In this first broad aspect of the invention, the high-selectivity, continuous processes for converting aldohexose in an aldohexose-yielding carbohydrate-containing feed to ethylene glycol comprise:

a. continuously or intermittently passing said carbohydrate feed into a reaction zone having an aqueous, hydrogenation medium containing retro-aldol catalyst, hydrogen and hydrogenation catalyst;

b. maintaining the aqueous, hydrogenation medium in the reaction zone at hydrogenation conditions to provide a product solution comprising ethylene glycol, propylene glycol and hexitol, said hydrogenation conditions comprising a temperature in the range of between about 230° C. to 300° C., a ratio of retro-aldol catalyst to hydrogenation catalyst, and hydrogen partial pressure that, in combination, are sufficient to:
  i. convert at least about 95 percent of the aldohexose-yielding carbohydrate,
  ii. provide a conversion efficiency of said aldohexose to ethylene glycol of at least about 60 percent, and
  iii. provide a mass ratio of ethylene glycol to hexitol greater than about 10:1 in the product solution; and
c. continuously or intermittently withdrawing product solution from said reaction zone,
wherein said carbohydrate feed is at least partially hydrated and is under a pressure sufficient to maintain partial hydration; wherein said carbohydrate feed is below a temperature of about 170° C.; and wherein said carbohydrate feed is heated to above 230° C. immediately prior to or in the reaction zone and the rate of heating of the carbohydrate feed from below 170° C. to above 230° C. is sufficient to provide a product solution having at least one of:
  A. a mass ratio of ethylene glycol to propylene glycol from said aldohexose of at least about 15:1, and
  B. a mass ratio of glycerin to propylene glycol from said aldose of less than about 0.5:1

The carbohydrate feed may be admixed with retro-aldol catalyst prior to being heated to a temperature above 230° C. or may be substantially devoid of any retro-aldol catalyst. In some aspects of the invention, the carbohydrate feed will contain retro-aldol catalyst. In these aspects, retro-aldol reactions may occur during the heating. Because the carbohydrate feed is introduced into the aqueous, hydrogenation medium upon heating, any glycolaldehyde generated is promptly available for hydrogenation to ethylene glycol.

In yet a further expression of this first broad aspect of the invention, the high-selectivity, continuous processes for converting aldohexose in an aldohexose-yielding carbohydrate-containing feed to ethylene glycol comprise:
a. continuously or intermittently passing said carbohydrate feed into a reaction zone having an aqueous, hydrogenation medium containing retro-aldol catalyst, hydrogen and hydrogenation catalyst;
b. maintaining the aqueous, hydrogenation medium in the reaction zone at hydrogenation conditions to provide a product solution comprising ethylene glycol, propylene glycol, glycerin and hexitol, said hydrogenation conditions comprising a temperature in the range of between about 230° C. to 300° C., a ratio of retro-aldol catalyst to hydrogenation catalyst, and hydrogen partial pressure that, in combination, are sufficient to convert at least about 95 percent of the aldohexose-yielding carbohydrate; and
c. continuously or intermittently withdrawing product solution from said reaction zone,
wherein said carbohydrate feed is at least partially hydrated and is under a pressure sufficient to maintain partial hydration; wherein said carbohydrate feed is below a temperature of about 170° C.; and wherein said carbohydrate feed is heated at least in part by direct heat exchange with a warmer fluid to above about 230° C. immediately prior to or in the reaction zone and the rate of heating of the carbohydrate feed from below 170° C. to above 230° C. is sufficient to provide a product solution having at least one of:
  A. a mass ratio of glycerin to propylene glycol from said aldose of less than about 0.5:1, and
  B. a mass ratio of ethylene glycol to hexitol greater than about 20:1 and a mass ratio of ethylene glycol to propylene glycol from said aldohexose of at least about 15:1.

The warmer fluid for the direct heat exchange may be any suitable fluid and often comprises water. The temperature and amount of the warmer fluid are sufficient to enable the carbohydrate feed to achieve, in combination with any other heating source, a temperature of at least 230° C. Often, the warmer fluid is above 230° C., and in some instances above 235° C. The carbohydrate feed can be introduced into a reaction zone for the hydrogenation, or, if used, a prior retro-aldol reaction zone having an essential absence of hydrogenation catalyst, and the aqueous medium contained in such reaction zone serves as the warmer fluid. Alternatively, a warmer fluid may be combined with the carbohydrate feed prior to the combination being introduced into a retro-aldol or combination retro-aldol and hydrogenation reaction zone.

The commencement of the contact between the carbohydrate feed and the retro-aldol catalyst may occur in the reaction zone containing the hydrogenation catalyst or in a separate reaction zone. Where the contact is commenced in a separate reaction zone, all or a portion of the aldohexose can be reacted in the separate reaction zone. In some instances, all or a portion of the aldohexose undergoes retro-aldol conversion in the reaction zone containing the hydrogenation catalyst, e.g., at least about 10, and sometimes at least about 20, mass percent to essentially all of the aldohexose in the carbohydrate feed undergoes retro-aldol conversion in the reaction zone containing the hydrogenation catalyst. In the certain embodiments of the instantly disclosed processes, the retro-aldol catalyst is a homogeneous catalyst and the hydrogenation catalyst is heterogeneous. Thus, the dispersion of the retro-aldol catalyst within the region occupied by the hydrogenation catalyst can provide glycolaldehyde and other intermediates that can provide ethylene glycol proximate to hydrogenation sites.

The amount of hydrogenation catalyst required for a given circumstance will depend upon the relative activity of the catalyst and the mass transfer of hydrogen and glycolaldehyde and intermediates to the catalyst. A preferred hydrogenation catalyst is a supported nickel-containing hydrogenation catalyst, especially nickel catalysts containing one or both of rhenium and iridium. The ratio of the retro-aldol catalyst to hydrogenation catalyst is preferably sufficient that the production of hexitols, e.g., from the hydrogenation of aldohexose, is minimized. However, it is preferred that the hydrogenation catalyst have a density in the reaction zone sufficient to cause hydrogenation of glycolaldehyde and other intermediates before competitive reactions of glycolaldehyde and other intermediates are able to generate products other than ethylene glycol.

Preferably carbohydrate-containing feeds that provide between about 120 and 700 or 800, preferably between about 150 and 500, say, 200 to 400, grams total carbohydrate per liter of aqueous, hydrogenation medium to provide product solutions having advantageous ratios of ethylene glycol to propylene glycol and reduced co-production of 1,2-butanediol. Without wishing to be limited by theory, it is believed that glycolaldehyde generated by the retro-aldol conversion of aldohexose can form a dimer or other structure ("protected species") that has less reactivity under the hydrogenation conditions than does glycolaldehyde. Thus, at low concentrations of carbohydrate feed in an aqueous reaction media, mass transfer limitations exist that attenuate the production of protected species. Consequently, a greater portion of the glycolaldehyde generated can enter into competitive reactions with other components in the aqueous reaction medium. Conversely, at high concentrations of carbohydrate feed in an aqueous reaction medium, unreacted aldoses and other carbohydrates in the carbohydrate feed would increase the probability of contact with glycolaldehyde for competitive reactions or hydrogenation catalyst.

According to certain embodiments, the rate of the carbohydrate feed is in a range sufficient to provide a product solution having a mass ratio of 1,2-butanediol to ethylene glycol of less than about 1:30, and preferably less than about 1:50.

Each of the elements recited herein for each of the above broad aspects of this invention pertaining to processes for making ethylene glycol, to the extent not recited explicitly in other broad aspects of this invention are optional, or preferred, elements for the other broad processes of this invention.

Another broad aspect of the invention pertains to aqueous producer compositions comprising (excluding catalysts and water) containing ethylene glycol, propylene glycol, hexitol, glycerin and 1,2-butanediol wherein:
 a. ethylene glycol is present in an amount of at least about 70 mass percent,
 b. propylene glycol is present in a mass ratio of ethylene glycol to propylene glycol of between about 15:1 to 35:1,
 c. hexitol is present in a mass ratio of ethylene glycol to hexitol of greater than about 20:1,
 d. glycerin is present in a mass ratio of glycerin to propylene glycol of less than 0.5:1, and
 e. 1,2-butanediol is present in a mass ratio of 1,2-butanediol to ethylene glycol of less than about 1:30.

With respect to the above broad aspects of this invention, the carbohydrate feed contains an aldohexose-yielding carbohydrate. The aldohexose-yielding carbohydrate may be an aldohexose, per se, or may be a di- or polysaccharide that upon hydrolysis yields an aldohexose. Within the broad scope of this invention, the carbohydrate feed may also include a ketose-yielding carbohydrate or other aldose-yielding carbohydrate. In the instances where a ketose-yielding carbohydrate or other aldose-yielding carbohydrate is contained in the carbohydrate feed, a lower mass ratio of ethylene glycol to propylene glycol will result through the retro-aldol and hydrogenation reactions than that from a feed providing essentially only aldohexose. The processes of this invention also contemplate the addition of propylene glycol to the reactor. Nevertheless the ethylene glycol to propylene glycol mass ratio is that attributable to the aldohexose is preferably greater than 15:1.

In some instances, the carbohydrate feed can be a melted solid, in which case it should remain at least partially hydrated in order to avoid caramelization during the heating. Preferably the carbohydrate feed is provided as an aqueous solution.

BRIEF DESCRIPTION OF THE DRAWINGS

The Drawing is a schematic representation of a facility capable of using the process of this invention, according to certain embodiments.

DETAILED DESCRIPTION

All patents, published patent applications and articles referenced herein are hereby incorporated by reference in their entirety.

Definitions

As used herein, the following terms have the meanings set forth below unless otherwise stated or clear from the context of their use.

Where ranges are used herein, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3. 6.3, 0.815 and so forth) are included as are all intermediate ranges (e.g., 0.2-0.5, 0.54-0.913, and so forth).

The use of the terms "a" and "an" is intended to include one or more of the element described.

Admixing or admixed means the formation of a physical combination of two or more elements which may have a uniform or non-uniform composition throughout and includes, but is not limited to, solid mixtures, solutions and suspensions.

Aldose means a monosaccharide that contains only a single aldehyde group (—CH=O) per molecule and having the generic chemical formula $C_n(H2O)_n$. Non-limiting examples of aldoses include aldohexose (all six-carbon, aldehyde-containing sugars, including glucose, mannose, galactose, allose, altrose, idose, talose, and gulose); aldopentose (all five-carbon aldehyde containing sugars, including xylose, lyxose, ribose, and arabinose); aldotetrose (all four-carbon, aldehyde containing sugars, including erythrose and threose) and aldotriose (all three-carbon aldehyde containing sugars, including glyceraldehyde).

Aldose-yielding carbohydrate means an aldose or a di- or polysaccharide that can yield aldose upon hydrolysis. Most sugars are ring structures under ambient conditions and thus the aldose form occurs under the conditions of the process of this invention. Sucrose, for example, is an aldose-yielding carbohydrate even though it also yields ketose upon hydrolysis.

Aqueous and aqueous solution mean that water is present but does not require that water be the predominant component. For purposes of illustration and not in limitation, a solution of 90 volume percent of ethylene glycol and 10 volume percent water would be an aqueous solution. Aqueous solutions include liquid media containing dissolved or dispersed components such as, but not in limitation, colloidal suspensions and slurries.

Bio-sourced carbohydrate feedstock means a product that includes carbohydrates sourced, derived or synthesized from, in whole or in significant part, to biological products or renewable agricultural materials (including, but not limited to, plant, animal and marine materials) or forestry materials.

Commencing contact means that a fluid starts a contact with a component, e.g., a medium containing a homogeneous or heterogeneous catalyst, but does not require that all molecules of that fluid contact the catalyst.

Compositions of aqueous solutions are determined using gas chromatography for lower boiling components, usually components having 3 or fewer carbons and a normal boiling point less than about 300° C., and high performance liquid chromatography for higher boiling components, usually 3 or more carbons.

Conversion efficiency of aldohexose to ethylene glycol is reported in mass percent and is calculated as the mass of ethylene glycol contained in the product solution divided by the mass of aldohexose theoretically provided by the carbohydrate feed and thus includes any aldohexose per se contained in the carbohydrate feed and the aldohexose theoretically generated upon hydrolysis of any di- or polysaccharide contained in the carbohydrate feed.

Hexitol means a six carbon compound having the empirical formula of $C_6H_{14}O_6$ with one hydroxyl per carbon. Hexitols can have different stereoconfigurations, e.g., sorbitol and mannitol.

High shear mixing involves providing a fluid traveling at a different velocity relative to an adjacent area which can be achieved through stationary or moving mechanical means to affect a shear to promote mixing. As used herein, the components being subjected to high shear mixing may be immiscible, partially immiscible or miscible.

Hydraulic distribution means the distribution of an aqueous solution in a vessel including contact with any catalyst contained therein.

Immediately prior to means no intervening unit operation requiring a residence time of more than one minute exists.

Intermittently means from time to time and may be at regular or irregular time intervals.

Ketose means a monosaccharide containing one ketone group per molecule. Non-limiting examples of ketoses include ketohexose (all six-carbon, ketone-containing sugars, including fructose, psicose, sorbose, and tagatose), ketopentose (all five-carbon ketone containing sugars, including xylulose and ribulose), ketotetrose (all four-carbon, ketose containing sugars, including erythrulose), and ketotriose (all three-carbon ketose containing sugars, including dihydroxyacetone).

pH of an aqueous solution is determined at ambient pressure and temperature. In determining the pH of, for example the aqueous, hydrogenation medium or the product solution, the liquid is cooled and allowed to reside at ambient pressure and temperature for 2 hours before determination of the pH.

pH control agents means one or more of buffers and acids or bases.

A pressure sufficient to maintain at least partial hydration of a carbohydrate means that the pressure is sufficient to maintain sufficient water of hydration on the carbohydrate to retard caramelization. At temperatures above the boiling point of water, the pressure is sufficient to enable the water of hydration to be retained on the carbohydrate.

A rapid diffusional mixing is mixing where at least one of the two or more fluids to be mixed is finely divided to facilitate mass transfer to form a substantially uniform composition. Fractal mixing is a rapid diffusional mixing.

A reactor can be one or more vessels in series or in parallel and a vessel can contain one or more zones. A reactor can be of any suitable design for continuous operation including, but not limited to, tanks and pipe or tubular reactor and can have, if desired, fluid mixing capabilities. Types of reactors include, but are not limited to, laminar flow reactors, fixed bed reactors, slurry reactors, fluidized bed reactors, moving bed reactors, simulated moving bed reactors, trickle-bed reactors, bubble column and loop reactors.

Soluble means able to form a single liquid phase or to form a colloidal suspension.

Carbohydrate Feed

The processes of this invention use a carbohydrate feed that contains an aldohexose-yielding carbohydrate. In some instances, the carbohydrate feed comprises at least about 40, and preferably at least about 50, mass percent of aldohexose-yielding carbohydrate based upon total carbohydrate in the feed. Where product solutions containing a high mass ratio of ethylene glycol to propylene glycol are sought, the carbohydrate in the feed comprises at least about 90, preferably at least about 95 or 99, mass percent of aldohexose-yielding carbohydrate. Often the carbohydrate feed comprises a carbohydrate polymer such as starch, cellulose, or partially hydrolyzed fractions of such polymers or mixtures of the polymers or mixtures of the polymers with partially hydrolyzed fractions.

Most bio-sourced carbohydrate feedstocks yield glucose upon being hydrolyzed. The processes of this invention can be effectively used for the conversion of glucose and glucose precursors to ethylene glycol. Glucose precursors include, but are not limited to, maltose, trehalose, cellobiose, kojibiose, nigerose, nigerose, isomaltose, β,β-trehalose, α,β-trehalose, sophorose, laminaribiose, gentiobiose, and mannobiose. It is also acceptable to have glucose as a major portion or sole reactive component of the carbohydrate feed. Of course, other aldoses can be used in the processes of this invention. Other carbohydrate polymers and oligomers such as hemicellulose, partially hydrolyzed forms of hemicellulose, disaccharides such as sucrose, lactulose, lactose, turanose, maltulose, palatinose, gentiobiulose, melibiose, and melibiulose, or combinations thereof may be used. However, the nature of these may result in variable mixtures of ethylene glycol and propylene glycol.

The carbohydrate feed can be solid or in a liquid suspension or dissolved in a solvent such as water. Where the carbohydrate feed is in a non-aqueous environment, it is preferred that the carbohydrate is at least partially hydrated. Most preferably, the carbohydrate feed is provided in an aqueous solution. The mass ratio of water to carbohydrate in the carbohydrate feed is preferably in the range of 4:1 to 1:4. Aqueous solutions of 600 or more grams per liter of certain carbohydrates such as glucose and sucrose are sometimes commercially available. In some instances, recycle aqueous, hydrogenation solution or aliquot or separated portion thereof, may be contained in the carbohydrate feed. Where the carbohydrate feed contains ethylene glycol or propylene glycol, the mass ratio of total ethylene glycol and propylene glycol to carbohydrate is in the range of about 10:1 to 1:20, and sometimes in the range of about 2:1 to 1:20. It is within the purview of this invention to add water to the carbohydrate feed prior to introduction into the aqueous, hydrogenation medium. The carbohydrate contained in the carbohydrate feed is provided in an amount of between about 120 to 700 or 800, often, about 150 to 500, grams per liter of aqueous, hydrogenation medium. Optionally, a separate reaction zone can be used that contains retro-aldol catalyst with an essential absence of hydrogenation catalyst. Where a separate reaction zone containing retro-aldol catalyst is used, it is preferred that the carbohydrate contained in the carbohydrate feed to such reaction zone provide between about 120 to 700 or 800, often, about 150 and 500, grams of total carbohydrate per liter of aqueous medium in that separate zone.

Rapid Temperature Increase

In accordance with the first broad processes of this invention the carbohydrate feed is rapidly transitioned through the temperature zone of 170° C. to 230° C., and preferably to a temperature of at least about 240° C. The rapid heating to a temperature of at least 230° C. has been found by this invention to result in higher mass ratios of ethylene glycol to propylene glycol. The aldohexose-yielding carbohydrate in a carbohydrate feed provides a product solution having a mass ratio of ethylene glycol to propylene glycol of at least about 15:1, and sometimes at least about 20:1 and as high as 30:1 or more. Where the carbohydrate feed contains other aldose-yielding carbohydrates or ketose, propylene glycol is expected to result from the retro-aldol reaction and hydrogenation and this production of ethylene glycol and propylene glycol needs to be taken into account when determining the selectivity of conversion of aldohexose to ethylene glycol.

In some instances, the rapid heating through the temperature zone of 170° C. to 230° C. has been found to provide a relatively low mass ratio of glycerin to propylene glycol. In such instances, the mass ratio of glycerin to propylene glycol is often less than about 0.5:1. This mass ratio of glycerin to propylene glycol can be achieved regardless of whether the carbohydrate feed contains, in addition to aldohexose-yielding carbohydrate, other aldoses or ketoses. The low production of glycerin as a side product is advantageous due to the relatively low market value of glycerin as compared to ethylene glycol and propylene glycol.

The carbohydrate feed can be in the presence of other chemicals during the heating. For instance, hydrogen for the hydrogenation may be at least in part supplied with the carbohydrate feed. Other adjuvants, such as pH control agents, can also be present if desired. In one embodiment, the carbohydrate feed contains retro-aldol catalyst, and in such instances, catalytic conversion of the aldohexose-yielding carbohydrate occurs during the heating. The extent of conversion of the aldohexose-yielding carbohydrate during the heating will be affected, among other things, by the duration of the heating, the relative concentrations of the carbohydrate and the retro-aldol catalyst and the activity of the retro-aldol catalyst.

As discussed above, the heating of the carbohydrate feed can be accomplished in any suitable manner and one or more types of heating can be used. All, none, or a portion of the heating of the carbohydrate feed can occur before the carbohydrate feed is introduced into the aqueous, hydrogenation medium. For example, but not in limitation, the heating of the carbohydrate feed through the temperature zone of 170° C. to 230° C. can occur prior to introducing the aqueous, hydrogenation medium, and the heated carbohydrate feed can be maintained in contact with retro-aldol catalyst to effect conversion of the aldohexose-yielding carbohydrate to intermediates such as glycolaldehyde and erythrose for further conversion to ethylene glycol. In embodiments where the heated carbohydrate feed is maintained in contact with retro-aldol catalyst prior to being introduced into the aqueous, hydrogenation medium, the duration of such contact prior to introduction into the aqueous, hydrogenation medium is generally below about 15, preferably below about 10, and in some instances below about 5, seconds. Typically, any hold time prior to the introduction of the heated carbohydrate feed into the aqueous, hydrogenation medium is a consequence of the equipment configuration such as piping distances and residence time in ancillary equipment such as fluid distributors from the heat exchange zone into the hydrogenation zone. As can be appreciated, turn up and turn down operations will affect the inherent hold time.

The heat source used for the heating of the carbohydrate feed through the temperature zone of 170° C. to 230° C. is not critical. For instance, the heating can be provided by radiant or microwave excitation, indirect heat exchange with other process streams, or direct heat exchange with a process stream also passing to the aqueous, hydrogenation medium or combinations thereof. In instances where the carbohydrate feed through the temperature zone of 170° C. to 230° C. is heated at least in part by direct heat exchange with the aqueous, hydrogenation medium, it is generally preferred that retro-aldol catalyst is already present in the aqueous, hydrogenation medium. As discussed above, the rate of heating will be affected by heat and mass transfer parameters. It is generally desired to promote mixing of the carbohydrate feed during the heating to facilitate both mass and heat transfer and thereby reduce the time required for the carbohydrate feed to fully pass through this temperature zone. This mixing can be affected in any suitable manner including, but not limited to, mechanical and stationary mixing and rapid diffusional mixing. The thoroughness of the mixing also can affect the mass transfer of reactants, intermediates, catalysts and products and thus affect selectivities of conversion to ethylene glycol and the rate of formation of side products.

A particularly useful stream for direct heat exchange with the carbohydrate feed is withdrawn product solution (recycle). If a soluble retro-aldol catalyst is used in the aqueous, hydrogenation medium the recycle provides for a substantial return of the retro-aldol catalyst to the reaction system. The recycle can be at a temperature of at least about 180° C., say, at a temperature in the range of about 230° C. to 300° C. The mass ratio of recycle to carbohydrate feed will depend upon the relative temperatures of the two streams and the sought combined temperature. Often where a recycle is used, the mass ratio of recycle to carbohydrate feed is in the range of about 1:1 to 100:1. The recycle may be an aliquot portion of the withdrawn product solution, or may be subjected to unit operations to separate one or more components from recycle stream, such as, but not in limitation, degassing to remove hydrogen and filtration to remove, e.g., any entrained heterogeneous catalyst. Where the product solution is degassed to recover at least a portion of the hydrogen, the recycle is frequently an aliquot portion of the degassed product solution. One or more components can be added to the recycle prior to combination with the carbohydrate feed in the direct heat exchange in operation. These components include, but are not limited to, retro-aldol catalyst, pH control agents, and hydrogen. By using a recycle of withdrawn product solution, the combined carbohydrate feed and recycle can contain unreacted aldose-yielding carbohydrate, intermediates to ethylene glycol, and ethylene glycol. Where a carbohydrate feed is used which is not in aqueous solution, e.g., is a solid or is a melt, the recycle provides water to dissolve the carbohydrate and to stabilize the carbohydrate from caramelization.

The Conversion Process

The processes of this invention provide high conversion efficiency of aldose-yielding carbohydrate to ethylene glycol through retro-aldol and hydrogenation reactions. In the processes, the carbohydrate feed is introduced into an aqueous, hydrogenation medium that contains retro-aldol catalyst, hydrogen and hydrogenation catalyst. The carbohydrate feed may or may not have been subjected to retro-aldol conditions prior to being introduced into the aqueous, hydrogenation medium, and the carbohydrate feed may or may not have been heated through the temperature zone of 170° C. to 230° C. upon contacting the aqueous, hydrogenation medium. Thus, in some instances the retro-aldol reactions may not occur until the carbohydrate feed is introduced into the aqueous, hydrogenation medium, and in other instances, the retro-aldol reactions may have at least partially occurred prior to the introduction of the carbohydrate feed into the aqueous, hydrogenation medium. It is generally preferred to quickly disperse the carbohydrate feed in the aqueous, hydrogenation medium especially where the aqueous, hydrogenation medium is used to provide direct heat exchange to the carbohydrate feed. This dispersion can be achieved by any suitable procedure including, but not limited to, the use of mechanical and stationary mixers and rapid diffusional mixing.

The preferred temperatures for retro-aldol reactions are typically between about 230° C. and 300° C., and more preferably between about 240° C. and 280° C., although retro-aldol reactions can occur at lower temperatures, e.g., as low as 90° C. or 150° C. The pressures (gauge) are typically in the range of about 15 to 200 bar (1500 to 20,000 kPa), say, between about 25 and 150 bar (2500 and 15000 kPa). Retro-aldol reaction conditions include the presence of retro-aldol catalyst. A retro-aldol catalyst is a catalyst that catalyzes the retro-aldol reaction. Examples of compounds that can provide retro-aldol catalyst include, but are not limited to, heterogeneous and homogeneous catalysts, including catalyst supported on a carrier, comprising tungsten and its oxides, sulfates, phosphides, nitrides, carbides, halides and the like. Tungsten carbide, soluble phosphotungstens, tungsten oxides supported on zirconia, alumina and alumina-silica are also included. Preferred catalysts are provided by soluble tungsten compounds, such as ammonium metatungstate. Other forms of soluble tungstates, such as ammonium paratungstate, partially neutralized tungstic acid and sodium metatungstate. Without wishing to be limited to theory, the species that exhibit the catalytic activity may or may not be the same as the soluble tungsten compounds introduced as a catalyst. Rather, a catalytically active species may be formed in the course of the retro-aldol reaction. The concentration of retro-aldol catalyst used may vary widely and will depend upon the activity of the catalyst and the other conditions of the retro-aldol reaction such as acidity, temperature and concentrations of carbohydrate. Typically, the retro-aldol catalyst is provided in an amount to provide between about 0.05 and 100, say, between about 0.1 and 50, grams of tungsten calculated as the elemental metal per liter of aqueous, hydrogenation medium. The retro-aldol catalyst can be added as a mixture with the carbohydrate feed or as a separate feed to the aqueous, hydrogenation medium or both.

Where the carbohydrate feed is subjected to retro-aldol conditions prior to being introduced into the aqueous, hydrogenation medium, preferably the introduction into the aqueous, hydrogenation medium occurs in less than one, sometimes less than about 0.5, and in some instances less than about 0.1, minute from the commencement of subjecting the carbohydrate feed to the retro-aldol conditions. Often, at least about 10, preferably at least about 20, percent of the aldose-yielding carbohydrate in the carbohydrate feed is remaining upon introduction into the aqueous, hydrogenation medium. By continuing the retro-aldol conversions of the carbohydrate in the aqueous, hydrogenation medium, the duration of time between the retro-aldol conversion of the aldose to the commencement of contact with the hydrogenation catalyst is reduced.

Typically where aldose-yielding carbohydrate is present in the aqueous, hydrogenation medium the aqueous, hydrogenation medium is maintained at a temperature of at least about 230° C. until substantially all aldose-yielding carbohydrate is reacted. Thereafter, if desired, the temperature of the aqueous, hydrogenation medium can be reduced. However, the hydrogenation proceeds rapidly at these higher temperatures. Thus the temperatures for hydrogenation reactions are frequently between about 230° C. and 300° C., say, between about 235° or 240° C. and 280° C. The pressures (gauge) are typically in the range of about 15 to 200 bar (1500 to 20,000 kPa), say, between about 25 and 150 bar (2500 to 15,000 kPa). The hydrogenation reactions require the presence of hydrogen as well as hydrogenation catalyst. Due to the low solubility of hydrogen in aqueous solutions, the concentration of hydrogen in the aqueous, hydrogenation medium will primarily be determined by the partial pressure of hydrogen in the reactor. The pH of the aqueous, hydrogenation medium is often at least about 3, say, between about 3.5 and 8, and in some instances between about 4 and 7.5.

The hydrogenation is conducted in the presence of a hydrogenation catalyst. The hydrogenation catalyst can also be referred to as reducing metal catalysts and are catalysts for the reduction of carbonyls. Frequently the hydrogenation catalyst is a heterogeneous catalyst. It can be deployed in any suitable manner, including, but not limited to, fixed bed, fluidized bed, trickle bed, moving bed, slurry bed, and structured bed. Nickel, palladium and platinum are among the more widely used reducing metal catalysts. However many reducing catalysts will work in this application. The reducing catalyst can be chosen from a wide variety of supported transition metal catalysts. Nickel, Pt, Pd and ruthenium as the primary reducing metal components are well known for their ability to reduce carbonyls. One particularly favored catalyst for the reducing catalyst in this process is a Ni—Re catalyst supported on silica alumina. A similar version of Ni/Re or Ni/Ir can be used with good selectivity for the conversion of the formed glycolaldehyde to ethylene glycol. Nickel-rhenium is a preferred reducing metal catalyst and may be supported on alumina-silica, silica or other supports. Supported Ni—Re catalysts with B as a promoter are useful. Frequently in a slurry reactor, the hydrogenation catalyst is provided in an amount of between about 0.1 to 100, and more often, between about 0.5 or 1 and 50, grams per liter of aqueous, hydrogenation medium and in a packed bed reactor the hydrogenation catalyst comprises about 20 to 80 volume percent of the reactor.

Typically the retro-aldol reaction proceeds more quickly than the hydrogenation reaction and consequently the residence time of the carbohydrate feed in the hydrogenation reactor is selected to reflect the sought degree of hydrogenation. In some instances, the weight hourly space velocity is between about 0.01 and 20, and frequently between about 0.02 and 5, $hr^{-1}$ based upon total carbohydrate in the feed. In some instances it is desired to maintain the aqueous, hydrogenation medium is well dispersed to assure relatively uniform concentrations of intermediates to ethylene glycol therein.

The retro-aldol and hydrogenation environment can result in undesired reactions. See, for instance, the *Green Chem.* article cited in the Background section. Table 1 on page 697 and Table 4 on page 700 of the article reports the product composition from subjecting various aldoses to retro-aldol and hydrogenation conditions. The primary side products they report include sorbitol, erythritol, propylene glycol and glycerol. Not only do these side products represent a loss of conversion efficiency to ethylene glycol but also side products such as glycerol have an economic value lower than that of ethylene glycol. The side products can further be reacted under these conditions, and ethylene glycol degraded as reported in their Table 3. The formation of side products can in part be attributed to the generation of reactive species as intermediates, especially glycolaldehyde and erythrose.

In the processes of this invention, the combination of reaction conditions (e.g., temperature, hydrogen partial pressure, concentration of catalysts, hydraulic distribution, and residence time) are sufficient to convert at least about 95, often at least about 98, mass percent and sometimes essentially all of the aldohexose-yielding carbohydrate. It is well within the skill of the artisan having the benefit of the disclosure herein to determine the set or sets of conditions that will provide the sought conversion of the aldohexose-yielding carbohydrate. The processes of this invention also use a combination of conditions that can provide a conversion efficiency of the aldohexose to ethylene glycol of at least about 60, preferably at least about 70, and more preferably at least about 75, mass percent. The conversion efficiency to ethylene glycol is determined as the mass of ethylene glycol in the product solution as a percentage of the mass of aldohexose-yielding carbohydrate in the carbohydrate feed. Where the carbohydrate feed contains other carbohydrates, the contributions of the other feed to the ethylene glycol content are taken into account.

Without wishing to be limited by theory, it is believed that the formation of intermediates by the retro-aldol reaction needs to be in close time proximity to the hydrogenation of those intermediates to ethylene glycol such that they are hydrogenated before a significant amount of the intermediates can be consumed in competitive reactions. Accordingly, a balance between the retro-aldol catalyst and hydrogenation catalyst can be ascertained for a given retro-aldol catalyst and a given hydrogenation catalyst under the conditions of the reaction in order to achieve a high conversion efficiency to the ethylene glycol. Additionally it is believed that the rapid heating of the carbohydrate feed provides the feed at temperatures where the retro-aldol rate of reaction can be more easily matched to the hydrogenation rate of reaction.

It is believed that the ratio of the retro-aldol catalyst to hydrogenation catalyst can also serve to attenuate the production of hexitol by both minimizing the presence of carbohydrate and providing concentrations of intermediates to ethylene glycol that preferentially go to the active hydrogenation sites. One mode of operation of processes in accordance to certain embodiments uses a homogeneous retro-aldol catalyst and a heterogeneous hydrogenation catalyst such that retro-aldol catalyst can be physically located proximate to the hydrogenation catalyst. The intermediates, being smaller molecules, diffuse more rapidly to the catalyst sites than the larger carbohydrate molecules, and with the limited solubility of hydrogen in the aqueous, hydrogenation medium, hydrogen mass transfer rates to the hydrogenation catalyst are believed to modulate the hydrogenation reaction. Preferably the mass ratio of ethylene glycol to hexitol in the product solution is greater than about 10:1, and in some instances is greater than about 20:1 or 25:1 or even greater than about 40:1 or 50:1. As discussed above, providing total carbohydrate in the carbohydrate feed in an amount of about 120 to 700 or 800, or 150 to 500, grams per liter of aqueous, hydrogenation medium can serve to attenuate the rate of production of 1,2-butanediol.

Determining a suitable ratio of retro-aldol catalyst to hydrogenation catalyst is within the skill of the artisan having the benefit of the disclosures herein. The ratio will depend on, among other things, the relative activities of the two catalysts under steady-state conditions. The relative activities are influenced by the intrinsic activity of the catalysts, and the physical configuration of the catalysts. Hence, the ratios of these catalysts can vary widely over a range of retro-aldol catalysts and hydrogenation catalysts. However, for a given retro-aldol catalyst and hydrogenation catalyst, desirable ratios can be determined. If a retro-aldol reaction zone having an essential absence of hydrogenation catalyst is used, as taught by Schreck, et al., in U.S. Published Pat. Appl. 2015/0329449, the conditions, including, but not limited to, hydraulic residence time and retro-aldol catalyst concentration, can be adjusted to achieve the sought conversion efficiencies to ethylene glycol and mass ratios of ethylene glycol to sorbitol. If desired, the reaction zone containing the hydrogenation catalyst can have differing ratios of retro-aldol catalyst to hydrogenation catalyst. For example, in a continuous, stirred tank reactor using a homogeneous retro-aldol catalyst and a heterogeneous hydrogenation catalyst and the carbohydrate feed being introduced at or immediately below the surface of the aqueous, hydrogenation medium, the rate of stirring may be such that a density gradient for the hydrogenation catalyst exists. The lesser concentration of hydrogenation catalyst at the top of the aqueous, hydrogenation medium enables carbohydrates to be subjected to the retro-aldol reaction prior to significant amounts of hydrogenation occurring.

Post Reaction Processing

A product solution is withdrawn from the reaction zone continuously or intermittently. Following the reactor, a part of the withdrawn product solution may be separated for recycle back to the front of the process as described above. Preferably, at least a portion of the retro-aldol catalyst is recycled or recovered from the withdrawn product solution for recycle. The withdrawn product solution can be depressurized with the gases being captured for recovery of the hydrogen and removal of unwanted gaseous by-products such as methane and carbon dioxide.

Upon cooling, less soluble portions of catalysts that are solubilized from the bed or that are fed to the reactor are removed at the reduced temperature and the remaining liquid is transferred to the recovery portion of the process. Depending upon catalyst stability and solubility, it is possible to take the degassed reactor effluent to recovery where a portion of the volatile products are recovered and the heavy bottoms are treated for, e.g., recovery of the tungsten catalyst for reuse in the reactor.

In recovery the low boiling components such as ethanol and methanol are removed via distillation. Water is also removed via distillation followed by recovery of propylene glycol and ethylene glycol. It is typical in the manufacture of ethylene glycol to use multi-effected evaporators to minimize energy usage in the recovery of the ethylene glycol.

It is likely that separation of the ethylene glycol from the propylene glycol or other close boiling glycols will require an additional, more sophisticated separation technology. Simulated moving bed technology is one such option that can be used. The choice is dependent on the quality of the product that is required by the desired end use for the product.

Drawing

Reference is made to the drawing which is provided to facilitate the understanding invention but is not intended to be in limitation of the invention. The drawing is a schematic depiction of an apparatus generally designated as 100 suitable for practicing the instantly disclosed processes. The drawing omits minor equipment such as pumps, compressors, valves, instruments and other devices the placement of which and operation thereof are well known to those practiced in chemical engineering. The drawing also omits ancillary unit operations.

A carbohydrate feed is provided by line 102. The carbohydrate feed may be a solid or liquid including in a solution with water. For purposes of discussion, the carbohydrate feed is an aqueous glucose solution containing about 71 volume percent carbohydrate. A retro-aldol catalyst is provided via line 104. The addition of a retro-aldol catalyst is optional at this point in the process. For purposes of discussion, the retro-aldol catalyst is ammonium metatungstate in an aqueous solution, and the ammonium metatungstate is provided in an amount sufficient to have a concentration of ammonium metatungstate of about 10 grams per liter.

The carbohydrate feed is then combined with a warmer, recycle stream of withdrawn product solution as will be described later. This combination affects a direct heat exchange to increase the temperature of the carbohydrate feed and provide a combined stream. This combined stream then passes via line 106 to distributor 108 and reactor 110. Distributor 108 may be of any suitable design. For purposes of discussion, distributor 108 is spray head that distributes the combined stream as fine droplets over the surface of the aqueous, hydrogenation medium 112 in reactor 110. Reactor 110 contains agitator 114 to provide mechanical mixing of the aqueous, hydrogenation medium 112. This mechanical mixing assist in dispersing the fine droplets of the combined stream within the aqueous, hydrogenation medium to further enhance the rate that the combined stream is brought to the temperature of the aqueous, hydrogenation medium. It also assists in the mass transfer of intermediates from the retro-aldol reaction to the hydrogenation catalyst. Reactor 110 also contains a particulate, heterogeneous hydrogenation catalyst, by way of example, nickel/rhenium/boron hydrogenation catalyst on silica support, which catalyst is dispersed in the aqueous, hydrogenation medium by the mechanical mixing.

Hydrogen is supplied to reactor 110 through line 116. The hydrogen may be supplied through a nozzle to provide small bubbles of hydrogen to facilitate mass transfer of hydrogen into the aqueous, hydrogenation medium. If desired, an additional retro-aldol catalyst and other adjuvants may be supplied to the reactor the line 118.

Aqueous, hydrogenation medium is withdrawn from reactor 110 via line 120 as the product solution. As shown, a portion of the product solution is passed via line 122 to line 106 as recycle to be combined with the carbohydrate feed 102. This recycle will contain homogeneous retro-aldol catalyst. Optionally, the recycle stream in line 122 can be heated in indirect heat exchanger 124 to enable the combined stream in line 106 to have a higher temperature.

The following examples are provided to further illustrate the invention and are not in limitation of the invention. All parts and percentages are by mass unless otherwise stated.

Examples 1 to 20

The following general procedure is used in examples 1 to 20.

A 300 ml Hastelloy C Parr reactor is equipped with an agitator and one or two feed supply lines and a dip tube attached to a sample bomb. The end of the dip tube is positioned such that about 100 milliliters of solution would remain in the reactor. The reactor is charged with heterogeneous hydrogenation catalyst and an aqueous solution of tungsten-containing retro-aldol catalyst as specified in Table I. The charge is approximately 170 milliliters of aqueous solution. The reactor is then sealed and purged to remove oxygen. Purging is accomplished by three cycles of pressurizing the reactor to 50 psig (345 kPa gauge) with nitrogen, then venting to atmospheric pressure. The liquid level in the reactor is reduced to about 100 milliliters by draining through the dip tube. An additional three cycles of purging, while the aqueous solution is being stirred, are conducted using hydrogen to reduce the concentration of nitrogen, then venting to atmospheric pressure.

Stirring is commenced and is at a rate sufficient to maintain the heterogeneous hydrogenation catalyst in a slurry dispersion. The reactor is heated to reaction temperature as specified in Table I and pressurized under hydrogen to 10700 kilopascals gauge. When the reactor reaches operating temperature and pressure, feed of glucose solution is initiated and maintained at a constant rate for the duration of the run as is specified in Table I. Retro-aldol catalyst is continuously added at a constant rate for the duration of the run. Near-continuous operation is achieved by draining the reactor at regular intervals to a constant liquid level determined by the position of the dip tube. A filter attached to the end of the dip tube ensures all heterogeneous catalyst particles are retained inside the reactor. Every 10 to 15 minutes, the reactor pressure is adjusted to 10700 kilopascals by either adding hydrogen or venting.

A sample of the aqueous medium is taken during operation through the dip tube and sample bomb and cooled to room temperature. Typically the sample is taken after about 4 hours of operation although the sample in Example 16 is taken after about 1.6 hours, in Example 20, 2 hours, and in Example 3, after about 2 hours. The samples are analyzed by high pressure liquid chromatography (HPLC) and gas chromatography (GC). The HPLC is equipped with a refractive index detector and uses a Hi-Plex H resin column available from Agilent Technologies, Santa Clara, Calif. The GC analysis is performed with an HP 5890 GC (Agilent Technologies, Santa Clara, Calif.) using a flame ionization detector with 25:1 split injection. A J&W DB-WAX 30 m×0.32 mm×0.5 micron capillary column (Agilent Technologies, Santa Clara, Calif.) is used.

Except as otherwise stated, ammonium metatungstate is used as the precursor to the catalytically-active retro-aldol catalyst species. Unless otherwise stated, the hydrogenation catalyst is a nickel, rhenium and boron on silica alumina catalyst prepared using the procedure set forth at column 8, line 62, to column 9, line 27, of U.S. Pat. No. 6,534,441. The silica alumina support is a 3 millimeter extrudate and has a surface area of about 125 square meters per gram and a pore volume of about 0.7 to 0.9 milliliters per gram. The catalysts contain about 6.8 mass percent nickel, unless otherwise stated, and the mass ratio of the atoms of nickel:rhenium:boron is about 5:1.3:1.

In the examples, glucose is used as the carbohydrate feed and is provided at a concentration of about 32.4 mass percent in an aqueous solution except as otherwise noted. The glucose-containing feed contains, when a single feed supply line is use, retro-aldol catalyst. Where two feed supply lines, one is used for supplying the carbohydrate feed and the other is used to supply an aqueous solution of retro-aldol catalyst. The dimensions of the supply lines differ in inside diameter and length as well as positioning in the reactor. The supply lines that are used have either a ⅛ inch (3.2 millimeter) outside diameter or a 1/16 inch (1.6 millimeter) outside diameter. The length and diameter of the supply lines and their positioning affect the rate of heating of the carbohydrate feed as does the rate of flow through the supply lines. At a feed rate of 1 milliliter per minute, the residence time per 2.5 centimeters of length is about 0.4 second for a 1/16 inch supply line and about 3.7 seconds per 2.5 centimeters of length of a ⅛ inch supply line. Where two supply tubes are used, the feed rate in Table I is the sum of both feeds.

Comparative examples are designated by the abbreviation "comp" in Table I.

Table II summarizes the product compositions in each of the samples.

TABLE I

| Example | R-A Cat., mass % | Hydrog. Cat., grams | Temp., °C. | Feed rate, ml/min. | Feed system |
|---|---|---|---|---|---|
| 1 | 1.0 | 6 | 245 | 1 | Single 1/16 inch supply line 5 centimeters in length |
| 2 | 1.0 | 4 | 245 | 1 | Single 1/16 inch supply line 5 centimeters in length |
| 3 | 1.0 | 6 | 245 | 2 | Single 1/16 inch supply line 5 centimeters in length |
| 4 (comp)[a] | 1.0 | 6 | 245 | 1 | Single 1/16 inch supply line 5 centimeters in length |
| 5 | 0.25 | 6 | 245 | 1 | Single 1/16 inch supply line 5 centimeters in length |
| 6[b] | 1 | 6 | 245 | 1 | Single 1/16 inch supply line 5 centimeters in length |
| 7 | 0.25 | 6 | 255 | 1 | Single 1/16 inch supply line 5 centimeters in length |
| 8 | 0.1 | 6 | 245 | 1 | Single 1/8 inch supply line 10 centimeters in length |
| 9[c] | 1 | 6 | 245 | 1 | Single 1/8 inch supply line 10 centimeters in length |
| 10 (comp)[d] | 0.1 | 6 | 245 | 1 | Single 1/8 inch supply line 10 centimeters in length |
| 11 | 1 | 6 | 245 | 1 | Two supply lines, each 1/16 inch and 5 centimeters in length |
| 12 | 1 | 6 | 245 | 1 | Two supply lines, for carbohydrate feed, an insulated 1/16 inch 5 centimeters line, and for retro-aldol, 1/16 inch 10 centimeters line extending below the aqueous solution level |
| 13 | 1 | 6 | 245 | 1 | Two supply lines, each 1/8 inch by 10 centimeters |
| 14 (comp) | 0.5 | 6 | 225 | 1 | Single 1/8 inch supply line 5 centimeters in length |
| 15 | 1 | 2[e] | 245 | 1 | Single 1/8 inch supply line 5 centimeters in length |
| 16 | 0.5[f] | 2[e] | 245 | 2.5 | Single 1/8 inch supply line 5 centimeters in length |
| 17 | 1 | 6 | 245 | 1 | Single 1/16 inch supply line 5 centimeters in length (insulated to minimize heating of feed) |
| 18[g] | 1 | 6 | 245 | 0.9 | Single 1/8 inch supply line 5 centimeters in length |
| 19[g] | 1.5 | 6 | 245 | 0.9 | Single 1/8 inch supply line 5 centimeters in length |
| 20 | [h] | 6 | 245 | 2.5 | Single 1/8 inch supply line 5 centimeters in length |

[a] pressure is 5500 kilopascals gauge
[b] feed contains 31.6 mass percent glucose, 37 mass percent propylene glycol and water
[c] feed contains 32.4 mass percent glucose, 30 mass percent ethylene glycol and water
[d] feed contains 32.4 mass percent glucose, 30 mass percent ethylene glycol and water
[e] hydrogenation catalyst is ruthenium on carbon at a 5% loading (product number 206180) available from Sigma-Aldrich Chemical Company, St. Louis, Mo, U.S.A.
[f] sodium metatungstate is used
[g] feed contains 50 mass percent glucose
[h] 0.5 mass percent sodium metatungstate and 0.6 mass percent sodium tungstate

TABLE II

| Example | Conversion of Carbohydrate, mass % | Conversion Efficiency of Aldose to EG, mass % | EG:PG, mass | EG:Hexitol[a] mass | Glycerin:PG mass | 1,2-Butanediol, mass % |
|---|---|---|---|---|---|---|
| 1 | 100 | 79 | 29:1 | 150:1 | 0.3:1 | 1.3 |
| 2 | 100 | 85 | 29:1 | 100:1 | 0.3:1 | 1.3 |
| 3 | 100 | 70 | 17:1 | 58:1 | 0.4:1 | 1.9 |
| 4 (comp) | 100 | 37 | 10:1 | 370:1 | 0.3:1 | 2.2 |
| 5 | 100 | 77 | 24:1 | 27:1 | 0.6:1 | 1.3 |
| 6 | 100 | 86 | n/a[b] | 172:1 | n/a[b] | 1.4 |
| 7 | 100 | 64 | 20:1 | 320:1 | 0.3:1 | 1.7 |
| 8 | 100 | 68 | 15:1 | 26:1 | 0.6:1 | 2.0 |
| 9 | 100 | 72 | 15:1 | 180:1 | 0.2:1 | 3.0 |
| 10 (comp) | 100 | 63 | 15:1 | 27:1 | 0.6:1 | 2.0 |
| 11 | 100 | 80 | 28:1 | 160:1 | 0.2:1 | 1.6 |
| 12 | 100 | 83 | 34:1 | 410:1 | 0.2:1 | 1.1 |
| 13 | 100 | 73 | 16:1 | 240:1 | 0.2:1 | 1.7 |
| 14 (comp) | 100 | 54 | 9:1 | 11:1 | 0.6:1 | 4 |
| 15 | 100 | 76 | 24:1 | [c] | 0.3:1 | 1.7 |
| 16 | 100 | 69 | 17:1 | 110:1 | 0.4:1 | 2.5 |
| 17 | 100 | 83 | 26:1 | 410:1 | 0.2:1 | 1.9 |
| 18 | 100 | 79 | 17:1 | [c] | 0.2:1 | 3.2 |
| 19 | 100 | 82 | 20:1 | 820:1 | 0.6:1 | 2.6 |
| 20 | 100 | 68 | 16:1 | 92:1 | 0.5:1 | 1.5 |

[a] hexitol approximates sorbitol content
[b] not calculated due to PG in feed stream
[c] no hexitol is detected It is claimed:

1. A high-selectivity, continuous process for converting aldohexose in an aldohexose-yielding carbohydrate-containing feed to ethylene glycol comprising:

a. continuously or intermittently passing said carbohydrate-containing feed into a reaction zone having an aqueous, hydrogenation medium containing retro-aldol catalyst, hydrogen and hydrogenation catalyst;

b. maintaining the aqueous, hydrogenation medium in the reaction zone at hydrogenation conditions to provide a product solution comprising ethylene glycol, propylene glycol, glycerin and hexitol, said hydrogenation conditions comprising a temperature in the range of between about 230° C. to 300° C., a ratio of retro-aldol catalyst to hydrogenation catalyst, and hydrogen partial pressure that, in combination, are sufficient to:
  i. convert at least about 95 percent of the aldohexose-yielding carbohydrate,
  ii. provide a conversion efficiency of said aldohexose to ethylene glycol of at least about 60 percent, and
  iii. provide a mass ratio of ethylene glycol to hexitol greater than about 10:1 in the product solution; and
c. continuously or intermittently withdrawing product solution from said reaction zone, wherein said carbohydrate feed is at least partially hydrated and is under a pressure sufficient to maintain partial hydration; wherein said carbohydrate feed is below a temperature of about 170° C.; and wherein said carbohydrate feed is heated to above 230° C. immediately prior to or in the reaction zone and the rate of heating of the carbohydrate feed from below 170° C. to above 230° C. is sufficient to provide a product solution having at least one of:
  A. a mass ratio of ethylene glycol to propylene glycol from said aldohexose of at least about 15:1, and
  B. a mass ratio of glycerin to propylene glycol of less than about 0.5:1.

2. The process of claim 1 wherein the aldohexose-yielding carbohydrate being passed to the aqueous medium is in an aqueous solution.

3. The process of claim 2 wherein the aqueous solution contains retro-aldol catalyst.

4. The process of claim 3 wherein the aqueous solution is maintained at a temperature of greater than about 170° C. and less than 230° C. for less than about 15 seconds prior to being passed into the aqueous, hydrogenation medium.

5. The process of claim 4 wherein the aqueous solution contains retro-aldol catalyst at least during the heating from below 170° C. to above 230° C.

6. The process of claim 1 wherein the heating of the carbohydrate feed from below 170° C. to above 230° C. is at least in part by direct heat exchange by admixing the carbohydrate feed with a warmer fluid.

7. The process of claim 6 wherein the warmer fluid comprises the aqueous, hydrogenation medium.

8. The process of claim 6 wherein the admixing of the carbohydrate feed and warmer fluid involves high shear mixing.

9. The process of claim 6 wherein the admixing of the carbohydrate feed and warmer fluid involves rapid diffusional mixing.

10. The process of claim 6 wherein a portion of the withdrawn product solution is provided at a temperature of at least about 180° C. and is admixed with the carbohydrate feed prior to the carbohydrate feed being passed to the aqueous, hydrogenation zone.

11. The process of claim 10 wherein the portion of the recycled withdrawn product solution is an aliquot portion.

12. The process of claim 11 wherein the withdrawn product solution is degassed to remove at least a portion of the hydrogen to provide a degassed product solution, and then an aliquot portion of the degassed product solution is recycled.

13. The process of claim 1 wherein the heating of the carbohydrate feed from below 170° C. to above 230° C. is at least in part by indirect heat exchange.

14. The process of claim 1 wherein the heating of the carbohydrate feed from below 170° C. to above 230° C. occurs whereupon the carbohydrate is contacted with an aqueous, retro-aldol solution containing retro-aldol catalyst in the substantial absence of hydrogenation catalyst for a time sufficient to provide a the mass ratio of ethylene glycol to hexitol greater than about 25:1 in the product solution.

15. The process of claim 1 wherein the carbohydrate feed is in a solution containing at least one of ethylene glycol and propylene glycol in a mass ratio of total ethylene glycol and propylene glycol to carbohydrate is in the range of about 10:1 to 1:20.

16. The process of claim 1 wherein the carbohydrate-containing feed contains between about 120 and 800 grams of carbohydrate per liter of aqueous, hydrogenation medium.

17. A high-selectivity, continuous process for converting aldohexose in an aldohexose-yielding carbohydrate-containing feed to ethylene glycol comprising:
a. continuously or intermittently passing said carbohydrate feed into a reaction zone having an aqueous, hydrogenation medium containing retro-aldol catalyst, hydrogen and hydrogenation catalyst;
b. maintaining the aqueous, hydrogenation medium in the reaction zone at hydrogenation conditions to provide a product solution comprising ethylene glycol, propylene glycol, glycerin and hexitol, said hydrogenation conditions comprising a temperature in the range of between about 230° C. to 300° C., a ratio of retro-aldol catalyst to hydrogenation catalyst, and hydrogen partial pressure that, in combination, are sufficient to convert at least about 95 percent of the aldohexose-yielding carbohydrate; and
c. continuously or intermittently withdrawing product solution from said reaction zone, wherein said carbohydrate feed is at least partially hydrated and is under a pressure sufficient to maintain partial hydration; wherein said carbohydrate feed is below a temperature of about 170° C.; and wherein said carbohydrate feed is heated at least in part by direct heat exchange with a warmer fluid to above 230° C. immediately prior to or in the reaction zone and the rate of heating of the carbohydrate feed from below 170° C. to above 230° C. is sufficient to provide a product solution having at least one of:
  A. a mass ratio of glycerin to propylene glycol of less than about 0.5:1, and
  B. a mass ratio of ethylene glycol to hexitol greater than about 20:1 and a mass ratio of ethylene glycol to propylene glycol from said aldohexose of at least about 15:1.

18. The process of claim 17 wherein rate of heating is sufficient to raise the temperature of the entire carbohydrate feed from about 170° C. to at least 230° C. in less than about 5 seconds.

19. The process of claim 17 wherein rate of heating is sufficient to raise the temperature of the entire carbohydrate feed from about 170° C. to at least 230° C. in less than about 1 second.

* * * * *